(12) United States Patent
Cheung

(10) Patent No.: US 6,709,849 B2
(45) Date of Patent: Mar. 23, 2004

(54) DIETARY SUPPLEMENTS FOR REGULATING MALE HORMONE

(75) Inventor: Ling Yuk Cheung, New Territories (HK)

(73) Assignee: Ultra Biotech Limited, Douglas (GB)

( * ) Notice: Subject to any disclaimer, the term of this patent is extended or adjusted under 35 U.S.C. 154(b) by 0 days.

(21) Appl. No.: 10/187,113

(22) Filed: Jun. 28, 2002

(65) Prior Publication Data

US 2004/0001815 A1 Jan. 1, 2004

(51) Int. Cl.$^7$ .............................. C12N 1/14; C12N 13/00
(52) U.S. Cl. ............................... 435/173.1; 435/255.1; 435/255.2; 435/173.8
(58) Field of Search .......................... 435/173.1, 173.8, 435/255.1, 255.2

(56) References Cited

U.S. PATENT DOCUMENTS

| | | | |
|---|---|---|---|
| 4,081,367 A | 3/1978 | Hulls et al. .................. | 210/610 |
| 4,183,807 A | 1/1980 | Yoshizawa et al. ......... | 210/611 |
| 4,211,645 A | 7/1980 | Zajic et al. .................. | 210/611 |
| 4,559,305 A | 12/1985 | Zajic et al. .................. | 435/243 |
| 4,816,158 A | 3/1989 | Shimura et al. ............. | 210/610 |
| 5,075,008 A | 12/1991 | Chigusa et al. .............. | 210/610 |
| 5,106,594 A | 4/1992 | Held et al. ................... | 422/292 |
| 5,416,010 A | 5/1995 | Langenberg et al. ......... | 435/468 |
| 5,476,787 A | 12/1995 | Yokoyama et al. ....... | 435/262.5 |
| 5,567,314 A | 10/1996 | Chigusa et al. .............. | 210/150 |
| 5,578,486 A | 11/1996 | Zhang ......................... | 435/243 |
| 5,707,524 A | 1/1998 | Potter .......................... | 210/606 |
| 5,879,928 A | 3/1999 | Dale et al. ................... | 435/264 |
| 6,036,854 A | 3/2000 | Potter .......................... | 210/177 |
| 6,391,617 B1 | 5/2002 | Cheung ....................... | 435/254 |
| 6,391,618 B1 | 5/2002 | Cheung ....................... | 435/255 |
| 6,391,619 B1 | 5/2002 | Cheung ....................... | 435/255 |
| 6,436,695 B1 | 8/2002 | Cheung ....................... | 435/254 |
| 6,440,713 B1 | 8/2002 | Cheung ....................... | 435/173 |
| 2002/0123127 A1 | 9/2002 | Cheung ....................... | 435/254 |
| 2002/0123129 A1 | 9/2002 | Cheung ....................... | 435/254 |
| 2002/0123130 A1 | 9/2002 | Cheung ....................... | 435/262 |

FOREIGN PATENT DOCUMENTS

| | | |
|---|---|---|
| CN | 1110317 A | 10/1995 |
| EP | 0041373 | 12/1981 |
| FR | 2222433 | 10/1974 |
| JP | 60028893 | 2/1985 |
| RU | 415983 A | 11/1974 |
| RU | 1071637 | 2/1984 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/070682 A2 | 9/2002 |

OTHER PUBLICATIONS

K. Asami et al., "Real–Time Monitoring of Yeast Cell Division by Dielectric Spectroscopy", *Biophysical Journal*, 76, pp. 3345–3348 (1999).

E.K. Balcer–Kubiczek et al., "Expression Analysis of Human HL60 Cells Exposed to 60 Hz Square–or–Sine–Wave Magnetic Fields", *Radiation Research*, 153, pp. 670–678 (2000).

C.A.L. Basset et al., "Beneficial Effects of Electromagnetic Fields", *Journal of Cellular Biochemistry*, 51, pp. 387–393 (1993).

P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).

E.M. Goodman et al., "Effects of Electromagnetic Fields on Molecules and Cells", *International Review of Cytology*, 158, pp. 279–339 (1995).

T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

W. Grundler et al., "Nonthermal Effects of Millimeter Microwaves on Yeast Growth", *Z. Naturforsch*, 33, pp. 15–22 (1978).

W. Grundler et al., "Mechanisms of Electromagnetic Interaction with Cellular Systems", *Naturwissenschaften*, 79, pp. 551–559 (1992).

O.I. Ivaschuk et al., "Exposure of Nerve Growth Factor–Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

F. Jelinek et al., "Microelectronic Sensors for Measurement of Electromagnetic Fields of Living Cells and Experimental Results", *Bioelectrochemistry and Bioenergetics*, 48, pp. 261–266 (1999).

A. Lacy–Hulbert et al., "Biological Responses to Electromagnetic Fields", *FASEB Journal*, 12, pp. 395–420 (1998).

C.R. Libertin et al., "Effects of Gamma Rays, Ultraviolet Radiation, Sunlight, Microwaves and Electromagnetic Fields on Gene Expression Mediated by Human Immunodeficiency Virus Promotor", *Radiation Research*, 140, pp. 91–96 (1994).

H. Lin et al., "Specific Region of the c–myc Promoter is Responsive to Electric and Magnetic Fields", *Journal of Cellular Biochemistry*, 54, pp. 281–288 (1994).

(List continued on next page.)

*Primary Examiner*—Chris Tate
*Assistant Examiner*—Randall Winston
(74) *Attorney, Agent, or Firm*—Fish & Neave; James F. Haley, Jr.; Z. Ying Li

(57) ABSTRACT

Compositions comprising a plurality of yeast cells, wherein said plurality of yeast cells are characterized by their ability to treat male hormone deficiency in a subject as a result of having been cultured in the presence of an alternating electric field having a specific frequency and a specific field strength. Also included are methods of making such compositions.

9 Claims, 2 Drawing Sheets

OTHER PUBLICATIONS

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp. 679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low–Frequency Magnetic Fields Does Not Elevate MYC Steady–State mRNA Levels", *Radiation Research*, 153, pp. 663–669 (2000).

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects on DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic Field", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1054–1064 (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

Binninger, D. M. et al., "Effects of 60Hz AC magnetic fields–on gene expression following exposure over multiple cell generations using *Saccharomyces cerevisiae*", *Bioelectrochemistry and Bioenergetics*, 43(1): 83–89 (1997).

Deguchi, T. et al., "Nylon biodegradation by lignin–degrading fungi", *Applied and Environmental Microbiology*, 63(1): 329–331 (1997).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material—relation to food processing", *Radiation Physics and Chemistry*, 45(4): 591–607 (1995).

Van Rensburg, P. et al., "Engineering yeast for efficient cellulose degradation", *Yeast*, 14(1): 67–76 (1998).

"*Saccharomyces cerevisiae* Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

DIETARY SUPPLEMENTS FOR REGULATING MALE HORMONE

FIELD OF THE INVENTION

The invention relates to compositions that can ameliorate or prevent male hormone deficiency and are useful as dietary supplements. These compositions contain yeast cells obtainable by growth in electromagnetic fields with specific frequencies and field strengths.

BACKGROUND OF THE INVENTION

Testosterone levels in men decline with age. Testosterone deficiency has been associated with hip fracture and reduced bone mass in older men. Testosterone replacement therapy has been used to improve the level of this hormone.

Among various remedies, a number of botanical preparations have been used to restore erectile function, including ginseng, Ginkgo biloba, yohimbine (*Pausinytalia yohimbe*), and muira puama (*Ptychopetoalum olacoides*), a South American plant. L-arginine, a precursor of nitric oxide, and androstenedione also have application in male sexual function. Males who received testosterone had a significant increase in bioavailable testosterone concentration, hematocrit, right hand muscle strength and osteocalcin concentration. Treatment with the estrogen antagonist tamoxifen has been also shown to increase serum levels of testosterone in both mammal and oligozoospermic men. In addition, the anti-estrogen clomiphene is used to treat decreased libido, hypogonadotrophic hypogonadism and associated infertility.

SUMMARY OF THE INVENTION

This invention is based on the discovery that certain yeast cells can be activated by electromagnetic fields having specific frequencies and field strengths to increase serum levels of testosterone. Compositions comprising these activated yeast cells can therefore be used for treating male hormone deficiency or associated diseases in a subject (e.g., a human).

This invention embraces a composition comprising a plurality of yeast cells that have been cultured in an alternating electric field having a frequency in the range of about 10500 to 12000 MHz (e.g., 11210–11250 MHz) and a field strength in the range of about 100 to 600 mV/cm (e.g., 150–520 mV/cm). The yeast cells are cultured for a period of time sufficient to activate said plurality of yeast cells to treat male hormone deficiency or associated diseases in a subject. For instance, the cultured yeast cells when ingested can stimulate the growth (e.g., by at least 10% such as 20%, 30%, 40%, 50%, one fold, five fold, ten fold, and fifteen fold) of the prostate, seminal vesicle, and glandulae preputiales, and increase (e.g., by at least 10% such as 20% and 200%) the secretion of testosterone in a mammal.

In one embodiment, the frequency and/or the field strength of the alternating electric field can be altered within the aforementioned ranges during said period of time. In other words, the yeast cells are exposed to a series of electromagnetic fields. An exemplary period of time is about 50–200 hours (e.g., 60–145 hours).

Also included in this invention is a composition comprising a plurality of yeast cells that have been cultured under acidic conditions in an alternating electric field having a frequency in the range of about 11000 to 12000 MHz (e.g., 11200–11250 MHz) and a field strength in the range of about 200 to 600 mV/cm (e.g., 240–520 mV/cm). In one embodiment, the yeast cells are exposed to a series of electromagnetic fields. An exemplary period of time is about 50–100 hours (e.g., 56–84 hours).

Yeast cells that can be included in this composition are available from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. Box 2714, Beijing, 100080, China). Useful yeast species include, but are not limited to, those commonly used in food and pharmaceutical industries, such as *Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus, Saccharomyces sp., Schizosaccharomyces octosporus, Schizosaccharomyces pombe, Sporobolomyces roseus, Torulopsis candida, Torulopsis famia, Torulopsis globosa, Torulopsis inconspicua, Trichosporon behrendii, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii,* and *Saccharomycodes sinenses*. For instance, the yeast cells can be of the strain *Saccharomyces cerevisiae* Hansen AS2.375, AS2.501, AS2.502, AS2.503, AS2.504, AS2.535, AS2.558, AS2.560, AS2.561, AS2.562, or IFFI1048; or *Saccharomyces carlsbergensis* Hansen AS2.420 or AS2.444. Other useful yeast strains are illustrated in Table 1.

This invention further embraces a composition comprising a plurality of yeast cells, wherein said plurality of yeast cells have been activated to treat male hormone deficiency or associated diseases in a subject. Included in this invention are also methods of making these compositions.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
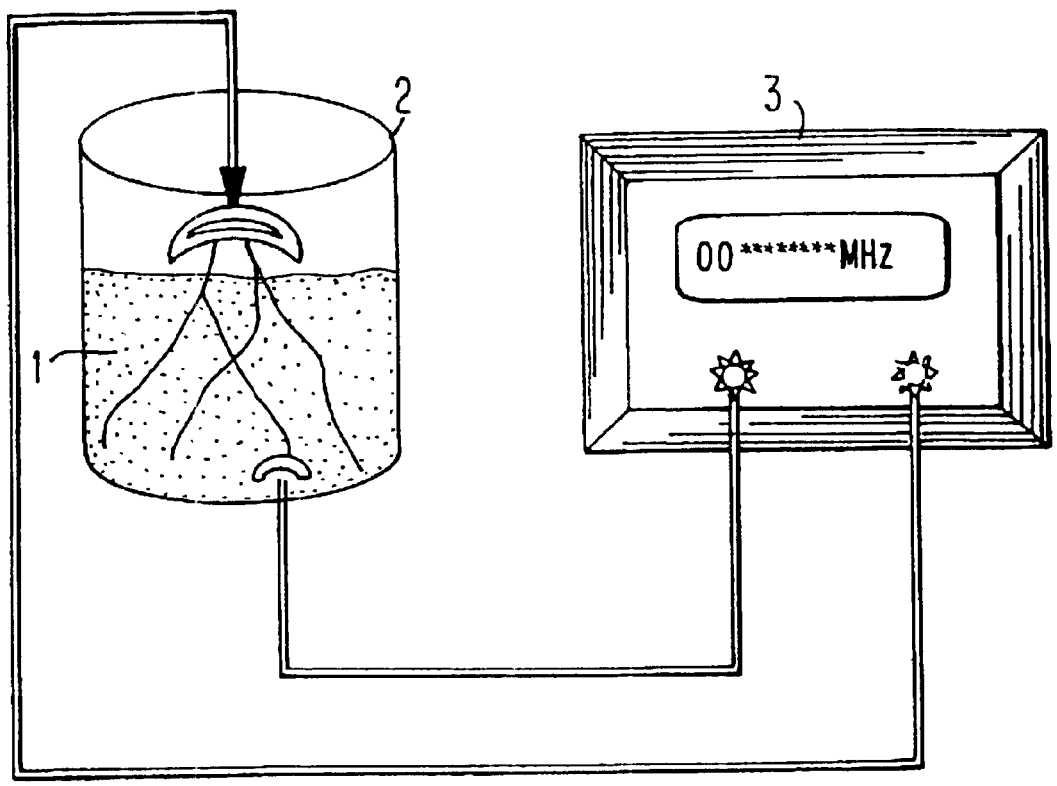
FIG. 1 is a schematic diagram showing an exemplary apparatus for activating yeast cells using electromagnetic fields. 1: yeast culture; 2: container, 3: power supply.

This invention is based on the discovery that certain yeast strains can be activated by electromagnetic fields ("EMF") having specific frequencies and field strengths to become highly efficient in producing substances that can increase serum levels of testosterone. Compositions containing these activated yeast cells are useful in the treatment of male hormone deficiency or associated diseases. Yeast compositions containing activated yeast cells can be used as dietary supplements in the form of health drinks or dietary pills.

Since the activated yeast cells contained in the yeast compositions have been cultured to endure acidic conditions (pH 2.5–4.2), these cells can survive the gastric environment and pass on to the intestines. Once in the intestines, the yeast cells are ruptured by various digestive enzymes, and the active substances are released and readily absorbed.

Without being bound by any theory or mechanism, the inventor believes that EMFs activate or enhance the expression of a gene or a set of genes or alter the conformation and/or activity of certain cellular components (e.g. DNA, RNA, enzymes/proteins) in the yeast cells, resulting in the production of agents that can ameliorate or prevent male hormone deficiency.

I. Yeast Strains Useful in the Invention

The types of yeasts useful in this invention include, but are not limited to, yeasts of the genera Saccharomyces, Candida, Crebrothecium, Geotrichum, Hansenula, Kloeckera, Lipomyces, Pichia, Rhodosporidium, Rhodotorula, Saccharomycodes, Schizosaccharomyces, Sporobolomyces, Torulopsis, Trichosporon, and Wickerhamia.

Exemplary species within the above-listed genera include, but are not limited to, *Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus,* Saccharomyces sp., *Schizosaccharomyces octosporus, Schizosaccharomyces pombe, Sporobolomyces roseus, Torulopsis candida, Torulopsis famta, Torulopsis globosa, Torulopsis inconspicua, Trichosporon behrendii, Trichosporon capitatum, Trichosporon cutaneum, Wickerhamiafluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii,* and *Saccharomycodes sinenses.*

Yeast strains useful for this invention can be obtained from laboratory cultures, or from publically accessible culture depositories, such as CGMCC and the American Type Culture Collection, 10801 University Boulevard, Manassas, Va. 20110–2209. Non-limiting examples of useful strains (with accession numbers of CGMCC) are *Saccharomyces cerevisiae* Hansen AS2.375, AS2.501, AS2.502, AS2.503, AS2.504, AS2.535, AS2.558, AS2.560, AS2.561, AS2.562 and EFFI1048; and *Saccharomyces carlsbergensis* Hansen AS2.420 and AS2.444. Other useful yeast strains are illustrated in Table 1.

Although it is preferred, the preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. ellipsoideus (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

AS2.131    AS2.213

*Saccharomyces delbrueckii*

AS2.285

*Saccharomyces delbrueckii* Lindner ver. mongolicus (Saito) Lodder et van Rij

AS2.209    AS2.1157

*Saccharomyces exiguous* Hansen

AS2.349    AS2.1158

*Saccharomyces fermentati* (Saito) Lodder et van Rij

AS2.286    AS2.343

*Saccharomyces logos* van laer et Denamur ex Jorgensen

AS2.156    AS2.327    AS2.335

*Saccharomyces mellis* (Fabian et Quinet) Lodder et kreger van Rij

AS2.195

TABLE 1-continued

Exemplary Yeast Strains

*Saccharomyces mellis* Microellipsoides Osterwalder

AS2.699

*Saccharomyces oviformis* Osteralder

AS2.100

*Saccharomyces rosei* (Guilliermond) Lodder et Kreger van Rij

AS2.287

*Saccharomyces rouxii* Boutroux

| | | | |
|---|---|---|---|
| AS2.178 | AS2.180 | AS2.370 | AS2.371 |

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

| | | | | |
|---|---|---|---|---|
| AS2.1207 | AS2.1216 | AS2.1220 | AS2.1379 | AS2.1398 |
| AS2.1399 | AS2.1400 | | | |

*Candida parapsilosis* (Ashford) Langeron et Talice Var. intermedia Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

| | | | |
|---|---|---|---|
| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| | | | | |
|---|---|---|---|---|
| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| | | |
|---|---|---|
| AS2.120 | AS2.281 | AS2.1180 |

*Crebrothecium ashbyii* (Guillermond) Routein (*Eremothecium ashbyii* Guilliermond)

| | | |
|---|---|---|
| AS2.481 | AS2.482 | AS2.1197 |

*Geotrichum candidum* Link

| | | | | |
|---|---|---|---|---|
| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| | | | | |
|---|---|---|---|---|
| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

*Hansenula schneggii* (Weber) Dekker

AS2.304

*Hansenula subpelliculosa* Bedford

| | | | | |
|---|---|---|---|---|
| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| | | | | |
|---|---|---|---|---|
| ACCC2022 | ACCC2023 | AS2.197 | AS2.496 | AS2.714 |
| ACCC2021 | AS2.711 | | | |

*Lipomycess starkeyi* Lodder et van Rij

| | |
|---|---|
| AS2.1390 | ACCC2024 |

*Pichia farinosa* (Lindner) Hansen

| | | | | |
|---|---|---|---|---|
| ACCC2025 | ACCC2026 | AS2.86 | AS2.87 | AS2.705 |
| AS2.803 | | | | |

*Pichia membranaefaciens* Hansen

| | | | |
|---|---|---|---|
| ACCC2027 | AS2.89 | AS2.661 | AS2.1039 |

*Rhodosporidium toruloides* Banno

ACCC2028

*Rhodotorula glutinis* (Fresenius) Harrison

| | | | | |
|---|---|---|---|---|
| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| | | | | |
|---|---|---|---|---|
| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| | | | | |
|---|---|---|---|---|
| AS2.102 | AS2.107 | AS2.278 | AS2.499 | AS2.694 |
| AS2.703 | AS2.704 | AS2.1146 | | |

*Saccharomyces carlsbergensis* Hansen

| | | | | |
|---|---|---|---|---|
| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| | | | | |
|---|---|---|---|---|
| IFFI1023 | IFFI1032 | IFFI1036 | IFFI1044 | IFFI1072 |
| IFFI1205 | IFFI1207 | | | |

*Saccharomyces willianus* Saccardo

| | | | | |
|---|---|---|---|---|
| AS2.5 | AS2.7 | AS2.119 | AS2.152 | AS2.293 |
| AS2.381 | AS2.392 | AS2.434 | AS2.614 | AS2.1189 |

*Saccharomyces sp.*

AS2.311

*Saccharomycodes ludwigii* Hansen

| | | |
|---|---|---|
| ACCC2044 | AS2.243 | AS2.508 |

*Saccharomycodes sinenses* Yue

AS2.1395

*Schizosaccharomyces octosporus* Beijerinck

| | |
|---|---|
| ACCC2046 | AS2.1148 |

*Schizosaccharomyces pombe* Lindner

| | | | | |
|---|---|---|---|---|
| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

*Sporobolomyces roseus* Kluyver et van Niel

| | | | | |
|---|---|---|---|---|
| ACCC2049 | ACCC2050 | AS2.19 | AS2.962 | AS2.1036 |
| ACCC2051 | AS2.261 | AS2.262 | | |

TABLE 1-continued

Exemplary Yeast Strains

*Torulopsis candida* (Saito) Lodder

| AS2.270 | ACCC2052 | | |
|---|---|---|---|
| *Torulopsis famta* (Harrison) Lodder et van Rij | | | |
| ACCC2053 | AS2.685 | | |
| *Torulopsis globosa* (Olson et Hammer) Lodder et van Rij | | | |
| ACCC2054 | AS2.202 | | |
| *Torulopsis inconspicua* Lodder et Kreger van Rij | | | |
| AS2.75 | | | |
| *Trichosporon behrendii* Lodder et Kreger van Rij | | | |
| ACCC2056 | AS2.1193 | | |
| *Trichosporon capitatum* Diddens et Lodder | | | |
| ACCC2056 | AS2.1385 | | |
| *Trichosporon cutaneum* (de Beurm et al.) Ota | | | |
| ACCC2057 | AS2.25 | AS2.570 | AS2.571 | AS2.1374 |
| *Wickerhamia fluorescens* (Soneda) Soneda | | | |
| ACCC2058 | AS2.1388 | | |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag-AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 10500 to 12000 MHz (e.g., 11210–11250 MHz). Exemplary frequencies are 11217, 11224, 11231, 11237, and 11244 MHz. The field strength of the electric field useful in this invention ranges from about 100 to 600 mV/cm (e.g., 150–230, 190–250, 250–270, 430–450, 430–450, or 480–520 mV/cm). Exemplary field strengths are 177, 221, 224, 236, 241, 244, 260, 442, 507, and 512 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above described ranges. Although any practical number of EMFs can be used in a series, it may be preferred that the yeast culture be exposed to a total of 2, 3, 4, 5, 6, 7, 8, 9 or 10 EMFs in a series.

Although the yeast cells can be activated after even a few hours of culturing in the presence of an EMF, it may be preferred that the activated yeast cells be allowed to multiply and grow in the presence of the EMF(s) for a total of 50–200 hours (e.g., 80–145 hours).

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 10 to 20,000 MHz. Signal generators capable of generating signals with a narrower frequency range can also be used. If desirable, a signal amplifier can also be used to increase the output. The activation container (2) can be made from non-conductive metal material, for example, plastics, glass steel, ceramic, and combinations thereof. The wire connecting the activation container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of electrode wires used depends on the volume of the culture as well as the diameter of the wires. The number of metal wires/tubes used can be from 1 to 10 (e.g., 2 to 3). It is recommended, though not mandated, that for a culture having a volume up to 10 L, metal wires/tubes having a diameter of 0.5 to 2.0 mm be used. For a culture having a volume between 10 L and 100 L, metal wires/tubes having a diameter of 3.0 to 5.0 mm can be used. For a culture having a volume in the range of 100–1000 L, metal wires/tubes having a diameter of 6.0 to 15.0 mm can be used. For a culture having a volume greater than 1000 L, metal wires/tubes having a diameter of 20.0 to 25.0 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy.

III. Culture Media

Culture media useful in this invention contain sources of nutrients assimilable by yeast cells. Complex carbon-containing substances in a suitable form, such as carbohydrates (e.g., sucrose, glucose, fructose, dextrose, maltose, xylose, cellulose, starches, etc.) and coal, can be the carbon sources for yeast cells. The exact quantity of the carbon sources utilized in the medium can be adjusted in accordance with the other ingredients of the medium. In general, the amount of carbohydrates varies between about 0.1% and 10% by weight of the medium, preferably between about 0.1% and 5%, and most preferably about 2%. These carbon sources can be used individually or in combination. Amino acid-containing substances in suitable form (e.g., beef extract and peptone) can also be added individually or in combination. In general, the amount of amino acid containing substances varies between about 0.1% and 1% by weight of the medium and preferably between about 0.1% and 0.5%. Among the inorganic salts which can be added to the culture medium are the customary salts capable of yielding sodium, potassium, calcium, phosphate, sulfate, carbonate, and like ions. Non-limiting examples of nutrient inorganic salts are $(NH_4)_2HPO_4$, $KH_2PO_4$, $K_2HPO_4$, $CaCO_3$, $MgSO_4$, NaCl, and $CaSO_4$.

IV. Electromagnetic Activation of Yeast Cells

The yeast cells of this invention can be activated by culturing in an appropriate medium under sterile conditions at 20° C.–38° C., preferably at 28–32° C. (e.g. 30° C.) for a sufficient amount of time, e.g., 80–200 hours (e.g., 103–145 hours), in an alternating electric field or a series of alternating electric fields.

An exemplary culture medium is made by mixing 1000 ml of distilled water with 20 g of sucrose, 50 μg of vitamin $B_6$, 40 μg of vitamin $B_{12}$, 0.20 g of $KH_2PO_4$, 0.2 g of $MgSO_4.7H_2O$, 0.25 g of NaCl, 0.1 g of $CaSO_4.2H_2O$, 3.0 g of $CaCO_3.5H_2O$, and 2.5 g of beef extract.

An exemplary set-up of the culturing process is depicted in FIG. 1. Untreated yeast cells are added to a culture medium at $1 \times 10^8$ cells per 1000 ml of the culture medium. The yeast cells may be Saccharomyces cerevisiae Hansen AS2.504, or may be selected from any of the strains listed in Table 1. An exemplary activation process of the yeast cells involves the following sequence: the yeast cells are allowed to grow in the culture medium for 35–45 hours (e.g., 42 hours) at 28–32° C. before being exposed to (1) an alternating electric field having a frequency of 11217 MHz and a field strength in the range of 190–250 mV/cm (e.g., 240–242 mV/cm) for 15–24 hours (e.g., 16 hours); (2) then to an alternating electric field having a frequency of 11224 MHz and a field strength in the range of 220–250 mV/cm (e.g., 235–237 mV/cm) for 12–24 hours (e.g., 22 hours); (3) then to an alternating electric field having a frequency of 11231 MHz and a field strength in the range of 430–450 mV/cm (e.g., 440–444 mV/cm) for 15–20 hours (e.g., 19 hours); (4) then to an alternating electric field having a frequency of 11237 MHz and a field strength in the range of 490–520 mV/cm (e.g., 505–509 mV/cm) for 15–20 hours (e.g., 17 hours); and (5) finally to an alternating electric field having a frequency of 11244 MHz and a field strength in the range of 210–230 mV/cm (e.g., 222–226 mV/cm) for 8–12 hours (e.g., 10 hours). The activated yeast cells are then recovered from the culture medium by various methods known in the art, dried (e.g., by lyophilization) and stored at about 4° C. in powder form. The resultant yeast power preferably contains more than $10^{10}$ cells/g.

V. Acclimatization of Yeast Cells To the Gastric Environment

Because the activated yeast cells of this invention must pass through the stomach before reaching the small intestine, where the effective components are released from these yeast cells, it is preferred that these yeasts be cultured under acidic conditions so as to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of 11237 MHz and a field strength in the range of 480–520 mV/cm (e.g., 510–514 mV/cm) at about 28 to 32° C. for 24–36 hours (e.g., 32 hours). The resultant yeast cells can then be further incubated in the presence of an alternating electric field having a frequency of 11244 MHz and a field strength in the range of 230–250 mV/cm (e.g., 242–246 mV/cm) at about 28 to 32° C. for 20–30 hours (e.g., 24 hours). The resulting acclimatized yeast cells are then recovered from the culture medium by various methods known in the art and are either dried and stored in powder form ($\geq 10^{10}$ cells/g) at room temperature or stored in vacuum at 0–4° C.

An exemplary acclimatizing culture medium is made by mixing 700 ml fresh pig gastric juice and 300 ml wild Chinese hawthorn extract. The pH of the acclimatizing culture medium is adjusted to 2.5 with 0.1 M hydrochloric acid (HCl) and/or 0.2 M potassium biphthalate ($C_6H_4$(COOK)COOH). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterile water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
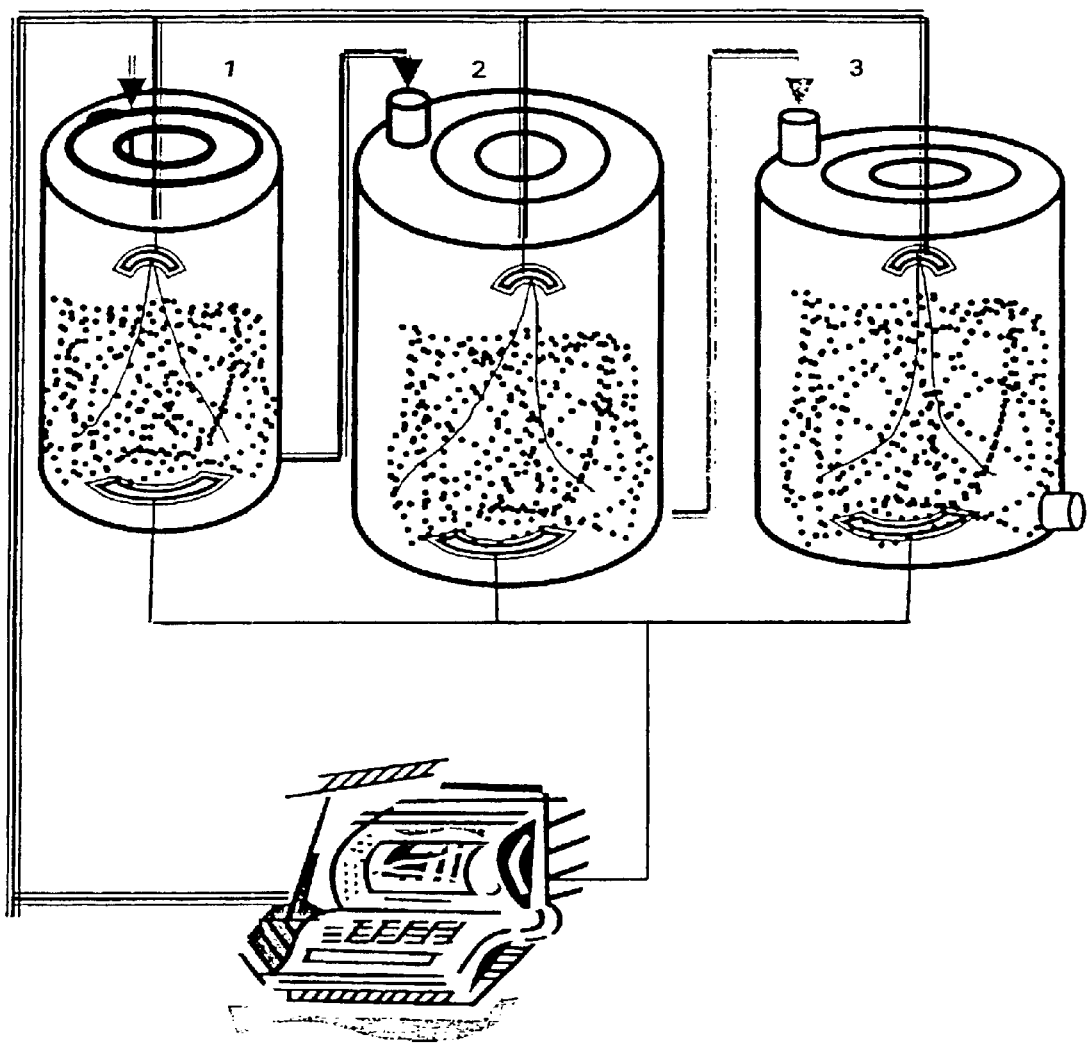
FIG. 2 is a schematic diagram showing an exemplary apparatus for making yeast compositions of the invention. The apparatus comprises a signal generator and interconnected containers 1, 2 and 3.

To prepare the yeast compositions of the invention, an apparatus depicted in FIG. 2 or an equivalent thereof can be used. This apparatus includes three containers, a first container (1), a second container (2), and a third container (3), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of Wu Wei Zi (*Schisandra chinensis* (Turez) Baill seeds) extract, and 100 L of soy bean extract. To prepare hawthorn, jujube and Wu Wei Zi extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and then centrifuged at 1000 rpm to remove insoluble residues. To make the culture medium, these extracts are mixed according to the above recipe, and the mixture is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (1) shown in FIG. 2. The yeast cells are then cultured in the presence of an alternating electric field having a frequency of 11237 MHz and a field strength of about 420–520 mV/cm (e.g., 510–514 mV/cm) at 28–32° C. under sterile conditions for 12 hours. The yeast cells are further incubated in an alternating electric field having a frequency of 11244 MHz and a field strength of 250–270 mV/cm (e.g., 258–562 mV/cm). The culturing continues for another 10 hours.

The yeast culture is then transferred from the first container (1) to the second container (2) which contains 1000 L of culture medium (if need be, a new batch of yeast culture can be started in the now available first container (1)), and subjected to an alternating electric field having a frequency of 11237 MHz and a field strength of 220–250 mV/cm (e.g., 233–237 mV/cm) for 12 hours. Subsequently the frequency and field strength of the electric field are changed to 11244 MHz and 215–240 mV/cm (e.g., 222–226 mV/cm), respectively. The culturing process continues for another 10 hours.

The yeast culture is then transferred from the second container (2) to the third container (3) which contains 1000 L of culture medium, and subjected to an alternating electric field having a frequency of 11237 MHz and a field strength of 150–230 mV/cm (e.g., 219–223 mV/cm) for 10 hours. Subsequently the frequency and field strength of the electric field are changed to 11244 MHz and 160–190 mV/cm (e.g., 175–179 mV/cm), respectively. The culturing continues for another 12 hours.

The yeast culture from the third container (3) can then be packaged into vacuum sealed bottles for use as dietary supplement, e.g., health drinks. If desired, the final yeast culture can also be dried within 24 hours and stored in powder form. The dietary supplement can be taken three to four times daily at 30–60ml/dose for a three-month period, preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound (1000 Hz) for 10 minutes and then centrifuged at 4355 g for another 10 minutes. The resulting supernatant is adjusted to pH 7.2–7.4 using 1 M NaOH and subsequently filtered through a membrane (0.22 μm for intravenous injection and 0.45 μm for peritoneal injection) under sterile conditions. The resulting sterile preparation is submerged in a 35–38 ° C. water bath for 30 minutes before use.

The yeast compositions of the present invention are derived from yeasts used in food and pharmaceutical industries. The yeast compositions are thus devoid of side effects associated with many pharmaceutical compounds.

VII. EXAMPLES

In order that this invention be more fully understood, the following examples are set forth. These examples are for the purpose of illustration only and are not to be construed as limiting the scope of the invention in any way.

The activated yeast compositions used in the following examples were prepared as described above, using *Saccharomyces cerevisiae* Hansen AS2.504, cultured in the presence of an alternating electric field having the electric field frequency and field strength exemplified in the parentheses following the recommended ranges listed in Section IV, supra. Control (i.e., untreated) yeast compositions were those prepared in the same manner as described in Section VI, supra, except that the yeast cells were cultured in the absence of EMFs. Unless otherwise indicated, the yeast compositions and the corresponding controls were administered to the animals by intragastric feeding.

Example 1

Effects of Yeast Compositions on Prostate, Seminal Vesicle and Glandulae Preputiales in Wistar Rats To test the ability of the EMF-treated AS2.504 cells to regulate male hormone, twenty-four healthy male Wistar rats (about 50 g body weight, 20 days old) were selected. Under ether anesthesia, both testes of each rat were removed under sterile conditions. The castrated rats were then randomly divided into four equal groups. The activated yeast composition was administered to Group A rats at a dose of 3 ml daily continuously for 14 consecutive days. The control yeast composition was administered to Group B rats at the same dosage. Testosterone propionate was injected intramuscularly to Group C rats in the buttocks at 25 mg/kg daily for 14 days. Saline was injected subcutaneously or intramuscularly to Group D rats at 2 ml/kg daily for 14 consecutive days.

Each rat was sacrificed 24 hours after the last administration of the composition of interest. The seminal vesicle and prostate were retrieved and placed in Bouin's Solution overnight. The fatty tissue around the prostate was removed. The ductus deferens, part of the urethra, and the bladder were also removed from the peripheries of the prostate. The remaining prostate was weighed and then submerged in 70% ethanol overnight. The urethra was completely stripped away from the prostate and seminal vesicle. The wet weight of the prostate and seminal vesicle was recorded (Table 2). The glandulae preputiales was also retrieved from the pubis area. The wet weight of the removed glandulae preputiales was also recorded (Table 2).

TABLE 2

Effects of Yeast Compositions on Prostate, Seminal Vesicle and Glandulae Preputiales in Wistar Rats

| Group | Compositions Administered | Prostate and Seminal Vesicle | Glandulae Preputiales |
|---|---|---|---|
| A | EMF-treated AS2.504 (3 ml daily) | 112.5 ± 14.6 | 120.9 ± 18.9 |
| B | unactivated AS2.504 (3 ml daily) | 42.6 ± 13.6 | 23.1 ± 11.4 |
| C | testosterone propionate (25 mg/kg daily) | 91.5 ± 12.8 | 98.6 ± 15.8 |
| D | saline (2 ml/kg daily) | 43.8 ± 5.8 | 22.7 ± 10.7 |

The results in Table 2 show that the composition comprising EMF-treated AS2.504 cells (1) was capable of stimulating the growth of prostate, seminal vesicle and glandulae preputiales, while the control yeast composition was not; and (2) was superior to testosterone propionate in stimulating the growth of prostate, seminal vesicle and glandulae preputiales.

Example 2

Effects of Yeast Compositions on Seminal Vesicle and Glandulae Preputiales in Mice Forty male NIH-grade castrated mice (about 25–30 g each) were randomly divided into four equal groups. Three days after castration, the activated yeast composition was administered to each of the Group A mice twice daily at 1.5 ml/dose for seven consecutive days. The control yeast composition was administered to each of the Group B mice at the same daily dosage for seven consecutive days. Testosterone propionate was injected intramuscularly to each of the Group C mice in the buttocks at 20 mg/kg every other day, i.e., on days 1, 3, 5, and 7, for a total of 7 days. Saline was orally administered to each of the Group D rats twice daily at 1.5 ml/dose for seven consecutive days.

Each mouse was sacrificed at the end of the treatment. Their seminal vesicles and glandulae preputiales were retrieved and the surrounding fatty tissue was stripped off. The seminal vesicles and glandular preputiales were weighed and the results are shown in Table 3.

TABLE 3

Effects of Yeast Compositions on Seminal Vesicle and Glandulae Preputiales in Mice

| Group | Seminal Vesicle (mg/100 g body weight) | Glandulae Preputiales (mg/100 g body weight) |
| --- | --- | --- |
| A | 361.3 ± 66.1 | 356.6 ± 61.2 |
| B | 39.1 ± 18.7 | 107.5 ± 41.2 |
| C | 268.2 ± 56.2 | 323.7 ± 50.6 |
| D | 38.6 ± 19.3 | 105.4 ± 37.6 |

The results in Table 3 show that the activated yeast composition (1) stimulated the growth of seminal vesicle and glandulae preputiales, while the control yeast composition did not; and (2) was superior to testosterone propionate in stimulating the growth of seminal vesicle and glandulae preputiales.

Example 3

Effects of Yeast Compositions on Testosterone Levels in Wistar Rats

To test the effect of the EMF-treated AS2.504 cells on the testosterone level, thirty-six healthy male Wistar rats (290±30 g) (10–12 months old) were randomly divided into six equal groups. Each rat was treated according to the procedure illustrated in Table 4.

TABLE 4

Treatment Procedure Used for Wistar Rats

| Group | Injection of Cyclophosphamide Five Days Prior to Administration (20 mg/kg) | Composition Administered and Duration |
| --- | --- | --- |
| $A_1$ | no injection | Activated yeast composition at 3 ml daily for 28 days |
| $B_1$ | no injection | Control yeast composition at 3 ml daily for 28 days |
| $A_2$ | injection | Activated yeast composition at 3 ml daily for 28 days |
| $B_2$ | no injection | Control yeast composition at 3 ml daily for 28 days |
| C | injection | distilled water at 20 ml/kg daily for 28 days |
| D | no injection | distilled water at 20 ml/kg daily for 28 days |

Each rat was sacrificed at the end of the treatment. Blood samples were collected from each rat, and the blood concentration of testosterone was determined by the standard radio-immunoassay (RIA) method. The results are shown in Table 5 below.

TABLE 5

Effects of Yeast Compositions on Testosterone Concentration in Wistar Rats

| Group | Testosterone Concentration (ng/dl) |
| --- | --- |
| $A_1$ | 206.3 ± 46.32 |
| $B_1$ | 146.12 ± 43.32 |
| $A_2$ | 172.42 ± 52.53 |
| $B_2$ | 89.11 ± 32.14 |
| C | 87.31 ± 23.51 |
| D | 145.28 ± 34.24 |

The results in Table 5 show that the activated yeast compositions increased the secretion of testosterone, while the control yeast composition did not.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to stimulate the growth of the prostate, seminal vesicle, and glandulae preputiales, and increase the secretion of testosterone in a subject as a result of having been cultured in the presence of an alternating electric field having a frequency in the range of 10500 to 12000 MHz and a field strength in the range of 100 to 600 mV/cm, as compared to yeast cells not having been so cultured.

2. The composition of claim 1, wherein said frequency is in the range of 11217 to 11244 MHz.

3. The composition of claim 1, wherein said field strength is in the range of 150 to 520 mV/cm.

4. The composition of claim 1, wherein said yeast cells are cells of the species selected from the group consisting of Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus, Saccharomyces sp., Schizosaccharomyces octosporus, Schizosaccharomyces pombe, Sporobolomyces roseus, Torulopsis candida, Torulopsis famta, Torulopsis globosa, Torulopsis inconspicua, Trichosporon behrendii, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggii, Hansenula subpelliculosa, Kloeckera apiculata, Lipomytes starkeyi, Pichia farinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii, and Saccharomycodes sinenses.

5. The composition of claim 1, wherein said yeast cells are cells of the strain deposited at the China General Microbiological Culture Collection Center with an accession number selected from the group consisting of Saccharomyces cerevisiae Hansen AS2.375, AS2.501, AS2.502, AS2.503, AS2.504, AS2.535, AS2.558, AS2.560, AS2.561, AS2.562 and IFFI1048, and Saccharomyces carlsbergensis Hansen AS2.420 and AS2.444.

6. The composition of claim 1, wherein said composition is in the form of a tablet, powder, or a health drink.

7. The composition of claim 1, wherein said composition is in the form of a health drink.

8. A method for treating male hormone deficiency in a subject comprising administering orally to said subject a composition of claim 1.

9. A method of preparing a yeast composition, comprising culturing a plurality of yeast cells in the presence of an alternating electric field having a frequency in the range of 10500 to 12000 MHz and a field strength in the range of 100 to 600 mV/cm, wherein said composition is capable of treating male hormone deficiency in a subject as compared to yeast cells not having been so cultured.

* * * * *